(12) United States Patent
Yarovesky (10) Patent No.: US 8,377,500 B2
(45) Date of Patent: *Feb. 19, 2013

(54) PROCESS FOR MAKING A DENTAL RESTORATION AND RESULTANT APPARATUS

(76) Inventor: Uriel Yarovesky, Thousand Oaks, CA (US)

(*) Notice: Subject to any disclaimer, the term of this patent is extended or adjusted under 35 U.S.C. 154(b) by 430 days.

This patent is subject to a terminal disclaimer.

(21) Appl. No.: 12/360,460

(22) Filed: Jan. 27, 2009

(65) Prior Publication Data

US 2009/0191511 A1    Jul. 30, 2009

Related U.S. Application Data

(63) Continuation-in-part of application No. 12/115,967, filed on May 6, 2008.

(60) Provisional application No. 61/024,498, filed on Jan. 29, 2008.

(51) Int. Cl.
*B05D 3/06* (2006.01)

(52) U.S. Cl. ............... 427/2.29; 433/203.1; 433/223; 264/19

(58) Field of Classification Search ......... 427/2.29; 433/203.1, 233, 29, 223; 264/19
See application file for complete search history.

(56) References Cited

U.S. PATENT DOCUMENTS

| 4,207,678 A | 6/1980 | Jeannette |
| 4,657,399 A | 4/1987 | Hall |
| 4,802,850 A | 2/1989 | Boon |
| 4,828,117 A | 5/1989 | Panzera et al. |
| 5,004,417 A | 4/1991 | Giaramita |
| 5,114,340 A | 5/1992 | Hahn |
| 5,240,414 A | 8/1993 | Thompson |
| 5,529,492 A | 6/1996 | Yarovesky et al. |
| 6,893,258 B1* | 5/2005 | Kert ............... 433/29 |
| 2003/0152733 A1* | 8/2003 | Wittmeyer, Jr. ........ 428/40.1 |
| 2005/0074721 A1* | 4/2005 | Kim ............... 433/208 |
| 2007/0081838 A1* | 4/2007 | Banhazl ............ 399/342 |
| 2007/0246148 A1* | 10/2007 | Barnes ............. 156/89.11 |
| 2007/0259309 A1* | 11/2007 | West et al. .......... 433/29 |

* cited by examiner

*Primary Examiner* — Peter Szekely
(74) *Attorney, Agent, or Firm* — Kelly & Kelley, LLP (57) ABSTRACT

A process for making a dental restoration includes forming an image which represents a natural oral cavity characteristic. The image may be formed on a computer by an artist or by capturing a photograph of an oral cavity. The computer-based image may be modified with a computer-aided software program. Thereafter, the image is printed as a decal and attached to the dental restoration base. The decal and the dental restoration base are conditioned by a high intensity light or by being fired together in an oven in order to create a finished dental restoration having the desired oral cavity color and characteristics.

34 Claims, 9 Drawing Sheets

PROCESS FOR MAKING A DENTAL RESTORATION AND RESULTANT APPARATUS

BACKGROUND OF THE INVENTION

The present invention relates to a process for making a dental restoration and the resultant apparatus. More particularly, the present invention relates to a process for attaching a decal to a resultant dental appliance for creating a dental restoration having desired color and characteristics similar in appearance to natural teeth and/or oral tissue.

Dental restorations, in general, are fabricated to replicate the natural anatomical appearance in the oral cavity. This fabrication process is highly dependent on the artistic abilities of dental technicians. This dependence creates a difficulty among dental laboratory owners and dentists to produce consistent quality for patients. The reason for this difficulty lies in the fact that there are relatively few dental technicians that have the artistic ability or experience to artistically perform dental restorations to a level necessary to achieve high aesthetic results. This creates a high demand for experienced dental technicians and correspondingly drives up costs as there are few dental technicians with the requisite experience. Such high costs make it difficult for laboratories to stay competitive in a global market.

A current dental restoration trend is to use veneers, which are a thinner, more conservative tooth restoration. These restorations are applied with the dentist removing little or no natural tooth structure. The sacrifice for this type of restoration is that, while the natural tooth stays relatively intact, the thin structure of the veneer provides little to no room for the laboratories to create the natural aesthetics that are achieved using three dimensional color and structures. Many patients do not understand the anatomy of a tooth and do not understand the importance of these structures in making smiles appear natural. Most dentists understand the importance of preserving the natural tooth for the purpose of maintaining sound structure. For this reason, some dentists may choose to make any necessary changes using minimally invasive dentistry. But, dentists are forced to use these thin veneers because of mass marketing to the public. Some dentists provide these restorations only to meet patient demand. The present invention endeavors to allow dentists to continue offering these conservative restorations without sacrificing the natural appearance of the restored tooth.

Thus, there is a need in the art for a process for making a dental restoration, and resultant apparatus, having desired color and characteristics similar to the natural oral cavity of which is applicable to crowns, bridges, ceramic restorations, resin, denture teeth, veneers, pre-fabricated matrixes, pre-cured resins and composites, and any other kind of restorative dental appliance. The present invention fulfills these needs and provides further related advantages.

SUMMARY OF THE INVENTION

The present invention is directed to a process for making a dental restoration and the resultant apparatus. The process for making the dental restoration includes the step of forming an image which represents a natural oral cavity characteristic. The natural oral cavity characteristic preferably comprises internal and external structures and coloration of teeth and oral cavity tissue, comprising teeth, enamel, dentin, crazing lines, stains, veins, blood vessels, bony coloration, hyper-calcification, mucosal tissue or gum tissue. Preferably, the step of forming the image includes the step of creating the image on a computer. In this regard, the image may be created digitally by hand by an artist or by capturing a digital photograph of an oral cavity. In one embodiment, the captured photograph is of the oral cavity of the patient receiving the dental restoration. In an alternative embodiment, the oral cavity photograph is of another person and is modified with a computer-aided software program to obtain the desired natural oral cavity characteristic. Furthermore, the process may include the step of colorizing the image to match the desired natural oral cavity characteristic of the patient receiving the dental restoration. Moreover, the forming step may also include the step of fabricating a stock set of standard images representative of select natural oral cavity characteristics a patient may receive. In this regard, a set of distributable pictures of the image may be created and matched to a decal printed from the image.

The printed decal is then attached to the dental restoration base. Accordingly, the decal and the dental restoration base are conditioned to create a finished dental restoration having the desired oral cavity color and characteristics. In one embodiment, the conditioning step may include the step of curing the decal and the dental restoration base with a high intensity light. In an alternative embodiment, the conditioning step includes the step of firing the decal and the dental restoration base in an oven. Moreover, the process for making a dental restoration base may further include the step of placing a sealant over the decal and at least a portion of the dental restoration base. Preferably, the sealant comprises a composite resin, a semi-transparent acrylic resin, a protective layer, a ceramic or a glaze. Thereafter, an additional secondary decal may be attached over the sealant. A glaze may then be applied over the secondary decal for protection thereof. Preferably, the dental restoration base comprises a composite resin, a veneer, an acrylic resin, a ceramic or a semi-transparent acrylic resin.

The resultant dental restoration apparatus includes a dental restoration base preferably made from a composite resin, a veneer, a ceramic or an acrylic resin. A decal attached to the dental restoration base has a select natural oral cavity characteristic and is preferably printed from a computer-based image. The computer-based image may comprise a photograph, a computer-generated model image or a drawing. The natural oral cavity characteristic may be painted to the computer-based image on a computer-aided software program. The natural oral cavity characteristic preferably comprises teeth, enamel, dentin, crazing lines, stains, veins, blood vessels, bony coloration, hyper-calcification, mucosal tissue or gum tissue. These natural oral cavity characteristics may be included in a stock of standard computer-based images representative of the natural oral cavity characteristics in the corresponding dental restoration. A distributable picture of the computer-based images matching the decal may also be provided so the patient may select the desired oral cavity characteristic prior to receiving the dental restoration. Additionally, a sealant is disposed over the decal and at least a portion of the dental restoration base for protection thereof. The sealant preferably comprises a composite resin, a semi-transparent acrylic resin, a protective layer, a ceramic or a glaze. An additional secondary decal may also be affixed to the sealant. Another layer of glaze may then be disposed over the secondary decal for protection thereof.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention resides in a process for making a dental restoration having a decal therein, and the resultant apparatus. The decals are designed to replicate the natural anatomical appearance of the oral cavity. Specifically, the decals are designed to replicate tooth coloration, crazing lines, internal coloration, hyper-calcification, transparency, enamel variation, veins, white stains, lines in teeth, and other tissue and tooth colorations artistically difficult to replicate.

Figure 1:
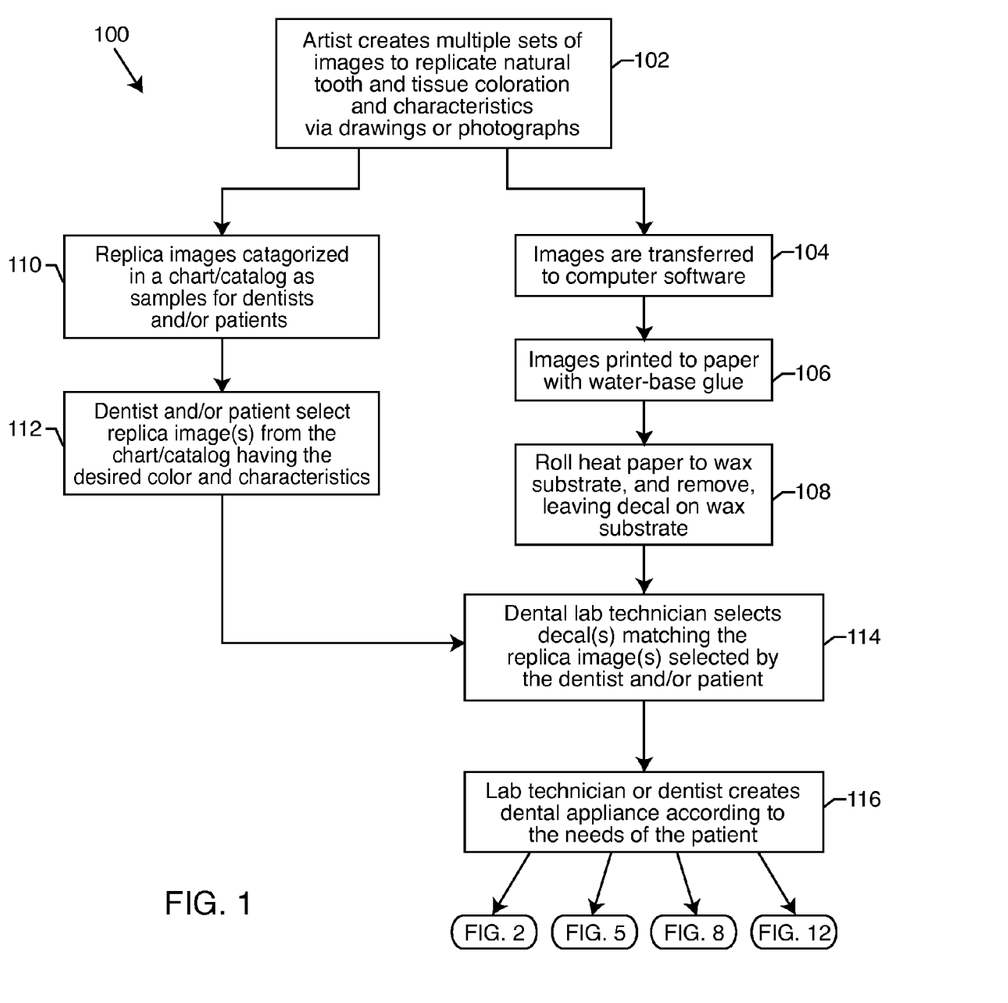
FIG. 1 is a flowchart illustrating the process of producing and selecting a decal for use in a dental appliance.

FIG. 1 illustrates a flowchart for a process of creating decals for placement in dental appliances (100). First, an artist creates multiple sets of images to replicate natural tooth and tissue coloration and characteristics (102). The images may be created via any one of a number of techniques that include manually drawing art work, photographs or computer generated images. In one embodiment, the decals may be made from artwork drawn out manually in a large format on an 8×10 sheet to provide accurate painted details of internal and external structures, characteristics and coloration of teeth and oral cavity tissue. The artist may choose to draw the decals based on photos of the patient, general photos of models, or drawings of internal and/or external tooth and oral cavity tissue. Alternatively, the artist may photograph the teeth of the patient to be later printed and used as the aforementioned decal. In this embodiment, the photographic image of the external structures, characteristics and coloration of the teeth and oral cavity tissue of the patient is not altered by the artist. In a similar sense, and a particularly preferred embodiment, the artist creates a set of decals by manipulating images in a digital-based computer aided software program to obtain the desired color and characteristics. The digital images may be those photographed of the patient or another person. The images may also be computer generated images developed completely by the artist through the related software program. The artist may manipulate the images through the computer aided software program to obtain the color and characteristics desired by the patient. Computer generated photographs are particularly preferred because the artist has the option of selecting one of many base or standard decals, making minor modifications to any of the base or standard decals, or using photographs of the oral cavity of the patient, including any desired modifications, to produce the most realistic and accurate decal specific to each individual patient receiving a dental restoration. Accordingly, the decals will vary in style, color, characteristics and may vary in size depending on the patient. The decals may include additional anatomical details such as mucosal tissue replication, veins, blood vessels, mimic bony coloring, hyper-calcification, crazing lines or any other natural or unnatural effects that affect tooth and oral cavity tissue color and characteristics. Appropriately, the decals will vary according to the application and desired use.

Once the details of the artwork are complete, the artwork is reduced in size to the size of natural teeth for dental application. The smaller size images are then transferred to computer software (104) suitable for printing the images to paper (106) having a water-based glue thereon. Next, the printed paper image is roll heated to a wax substrate (108). The decal remains on the wax substrate when the paper and wax substrate are subsequently separated. The decal on the wax substrate may comprise various color pigments to help correct tooth discoloration. The color pigment may even be opaque to facilitate blocking unwanted discoloration in cases where severe discoloration exists. The decals block out the darker background portion of a tooth to achieve lighter and brighter results. Alternatively, the color pigments of the decal may introduce desired color and structures within this layer. Accordingly, the printed decals are capable of being fired at recommended temperatures, to securely attach to the desired dental prosthesis. The versatility of such decals is virtually unlimited and can be used to recreate any type of dental effect, both existing structures and non-existing structures in the oral cavity.

Next, replica images are categorized in a chart and/or catalog as samples for viewing by dentists and/or patients (110). The catalog will include a variety of styles, colors and stylizations for the dentist to share with the patient in preparation for creating a dental restoration. The catalog is representative of the types of decals that are available at the dental laboratory, or any other facility where dental restorations are fabricated. Accordingly, the dentist and patient select a replica image or multiple replica images from the chart/catalog having the desired color and characteristics for the tooth or tissue restoration (112). The selected decal should have the appropriate color and transparency characteristics that match the natural oral cavity coloration and characteristics the patient desires. The dentist then communicates the selected decals to the dental lab technician at a facility that manufacturers the tooth restoration. From this information, the dental lab technician selects a decal, or multiple decals, matching the replica image, or multiple replica images, selected by the dentist and patient (114). The lab technician chooses the corresponding decals from the artist decal sheet to match the chosen images selected by the dentist and/or patient (112). The lab technician or dentist then creates the dental appliance according to the needs of the patient (116), as more specifically described in the flowcharts in FIGS. 2, 5, 9 and 13. Of course, the selected decal may include a standard or stock decal, a decal representative of a model tooth or a decal (modified or unmodified) created by photographing the oral cavity of the patient.

For standard or base decals, a reference catalog provided to dentists helps ensure the consistency and accuracy of selecting a particular style decal needed for the tooth restoration. Manufacturers and laboratories will have corresponding transparent decals that match the replica images selected by the dentist and/or patient. The decals are applied to the selected dental appliance. This method increases the aesthetic predictability of the appearance of the tooth restoration and virtually eliminates the difficult task of artistically mimicking the natural color and characterization of the oral cavity, one patient at a time. The present invention also reduces the need for training technicians to fabricate artistically realistic tooth restorations and transforms the manufacturing process into a much simpler technique, especially for ceramic teeth manufactured for use with dentures. As a result, the present invention will allow manufacturers to reduce the cost of tooling as multiple mold (more than 2) layering of the denture teeth will no longer be needed, thereby simplifying the methods of denture tooth fabrication.

Figure 2:
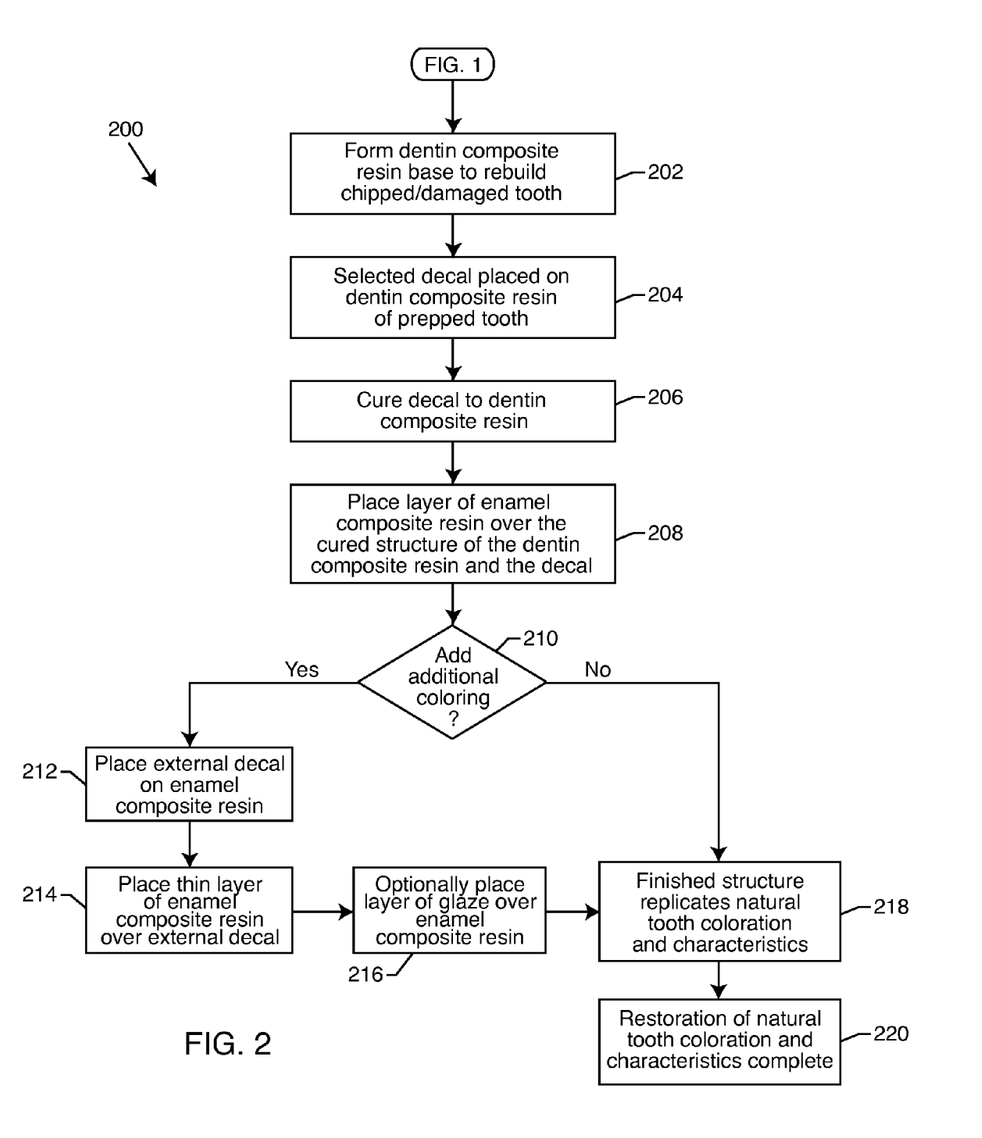
FIG. 2 is a flowchart illustrating the process of incorporating a decal in a composite resin-based dental restoration.

FIG. 2 illustrates a process for creating an oral cavity model or restoring a natural tooth, due to breakage, chipping or grinding (200). The first step is to apply a dentin colored composite resin to rebuild the chipped and/or damaged tooth (202). The dentin colored composite resin also forms the base of the oral cavity model. The dentin colored composite resin varies in coloration, but is commonly some shade yellow. For a damaged natural tooth, the dentin colored composite resin is placed in an appropriate location to create a fairly flat platform to allow the decals to conform to the surface thereof. Hardening the dentin colored composite resin is accomplished by any one of several polymerization processes. In one embodiment, the dentin colored composite resin is hardened using a halogen-based bulb that concentrates a specific wavelength of light on the composite resin. These bulbs are known in the dental industry and to those skilled in the art and are generally referred to as high intensity lights. A chemical catalyst in the composite resin is sensitive to the light. When exposed to the light, the composite resin hardens. A light-based hardening process may be accomplished chair side. Alternatively, non-chair side processes may include using pressure or heat to further harden the dentin colored composite resin. These hardening procedures are typically used to create model teeth or for replacement teeth for use in dentures or partials. Those teeth are normally fabricated out of an acrylic material or acrylic composite material or porcelain. In one embodiment, pressure is used to remove air gaps within the composite resin material to increase the density thereof thereby forming a harder structure than if only hardened by light. Accordingly, light may be used to further harden the structure by reacting with a chemical catalyst in the composite. In another alternative embodiment, the light and pressure is combined with heat. In this embodiment, the dentin colored composite resin achieves a high degree of polymerization at high intensity temperatures as high as 1700° F. Chemical catalysts in the composite resin react and harden at these high temperatures. Alternatively, the heating and pressurizing processes may be used exclusively without light. Different chemical compounds may be used in the composite resin depending on the desired polymerization process. Accordingly, the dentist or dental technician would endeavor to select the corresponding chemical catalyst that hardens in response to light, pressure or heat.

Next, the selected decal is placed on the hardened dentin composite resin of the prepped tooth (204). The decal is then cured to the dentin composite resin (206). To complete the initial contour and shape of the restored tooth, a layer of enamel composite resin is placed over the cured structure of the dentin composite resin and the decal (208). The dentist must then decide whether to add additional coloring (210). When adding additional coloring, an external decal is placed over the layer of enamel colored composite resin (212) to add the necessary stylizations to replicate the natural tooth colorizations and characteristics. Next, a thin layer of enamel composite resin is placed over the external decal (214). Thereafter, an optional layer of glaze is placed over the composite resin (216) to protect the dental restoration from possible long-term deterioration. The glaze is applied primarily to fill micro holes in the enamel composite resin and to enable the dentist to polish the outer surface of the tooth restoration. Decals can be used on external surfaces to achieve the desired colorization results. This application may also be used for pressable or milled ceramics for any ceramic restoration (tooth and oral tissue, such as mucosal tissue) that requires coloration variations where additional stylizations will enhance the overall aesthetic results of the tooth or tissue restoration, as further described herein. The completed structure should replicate the natural tooth coloration and characteristics (218) such that the restoration of the natural tooth coloration and characteristics is complete (220).

Figures 3, 4:
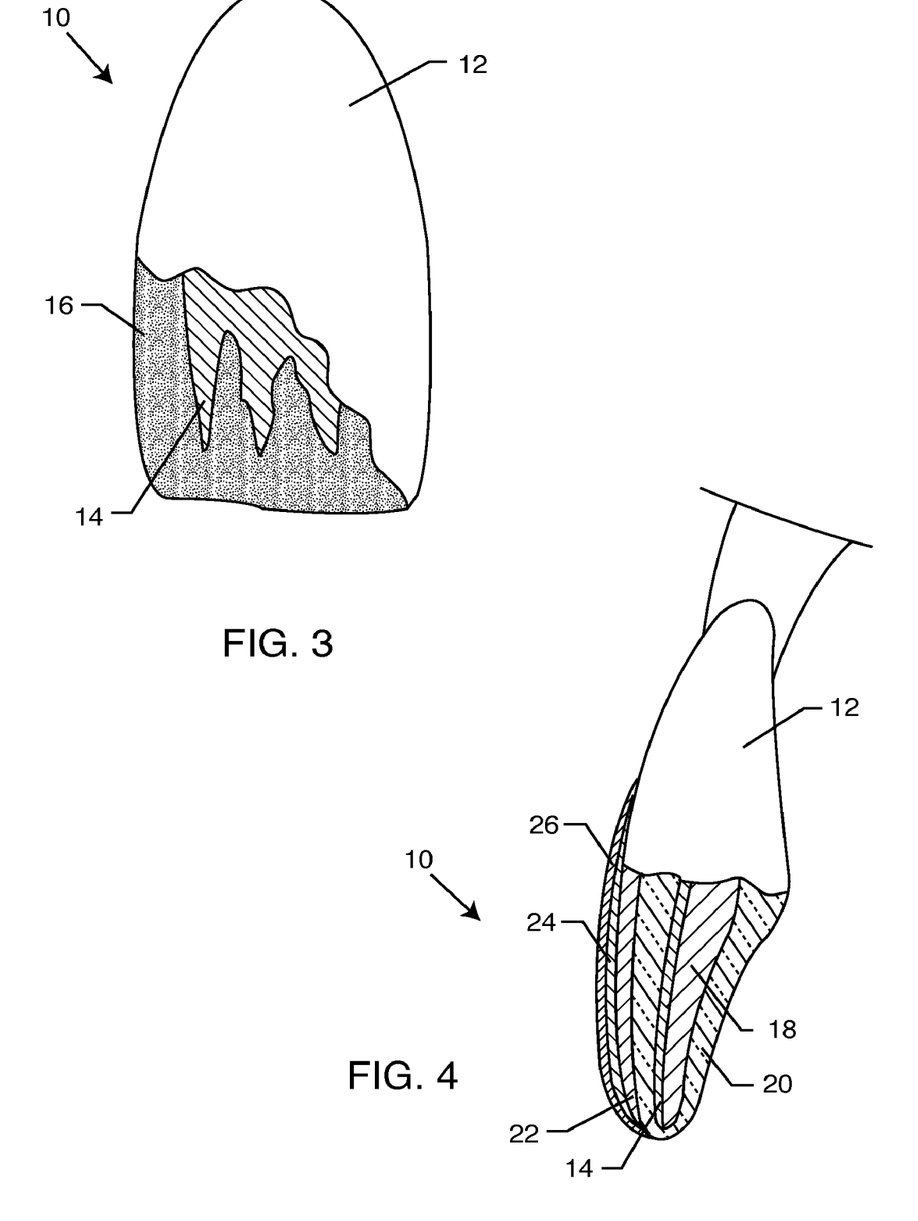
FIG. 3 is a front view of a rebuilt chipped tooth having a decal therein.
FIG. 4 is cross-sectional view of a restored chipped tooth, including an external decal having an enamel composite resin layer thereover.

FIGS. 3 and 4 illustrate a tooth restoration 10 of a chipped tooth 12 having a decal 14 therein. FIG. 3 is a front view of the tooth restoration 10 wherein a portion of the chipped tooth 12 is filled in with a filler 16. As shown in FIG. 4, the filler 16 comprises a dentin composite resin base 18 having the decal 14 formed thereon. Accordingly, after the decal is cured as described in step (206), an enamel composite resin 20 is disposed over the decal 14 and the dentin composite resin base 18. The filler 16 is designed to fix a cracked or broken portion of the tooth 12, generally shown in FIG. 3. The decal 14 is visible through the enamel composite resin 20 such that the colorization and characteristics of the decal 14 are viewable as shown through the front side of the chipped tooth 12 in FIG. 3. An additional external decal 22 may be disposed on top of the enamel composite resin 20 for additional coloring or characteristics. The external decal 22 may be protected by applying a thin layer of enamel composite resin 24 thereover. Optionally, a substantially transparent glaze 26 may be applied to the thin layer of enamel composite resin 24 for further protection thereof.

In an alternative embodiment, the tooth restoration 10 of FIGS. 3 and 4 could be used to create an oral cavity model. The model comprises similar compositions as the tooth restoration illustrated in FIG. 4. Of course, the model would not include a portion of the natural chipped tooth 12. Therefore, the dentin composite resin base 18, the enamel composite resin 20, the decal 14 and the thin enamel composite resin layer 24 would extend the entire length of the tooth restoration 10 as shown in partial form in FIG. 4. Likewise, the external decal 22 and optional glaze 26 should also extend the length of the tooth. The decal 14 or the external decal 22 may be applied as a whole sheet or as a series of partial sheets in sections of the front, back and bottom portions of the tooth. This process further ensures accurate replication of natural tooth colorization and characteristics.

Figure 5:
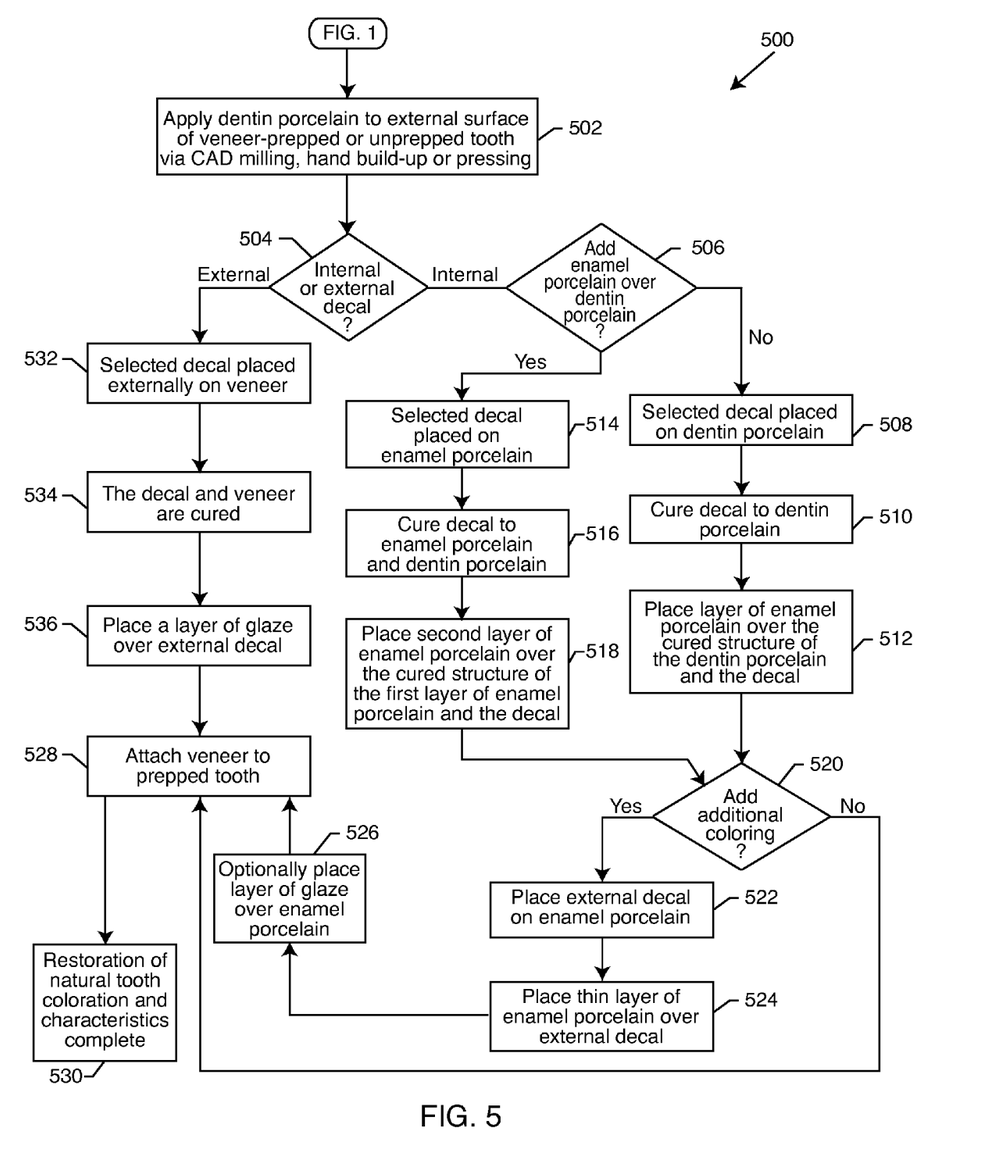
FIG. 5 is a flowchart illustrating the process of incorporating a decal into a veneer-based dental restoration.

Alternatively, the present invention may also be applied to composite resin-based or porcelain-based veneers. FIG. 5 illustrates a process for creating a tooth restoration using a decal and a porcelain-based veneer (500). The first step is to apply dentin porcelain to an external surface of the veneer-prepped tooth via CAD milling, hand build-up or pressing (502). Accordingly, step (502) involves shaving a portion of the existing tooth enamel down to make room for the necessary depth of the veneer. Prepping a tooth for veneer placement is well-known in the art. Alternatively, the dentin porcelain may be applied to an unprepped tooth. In this embodiment, a portion of the existing tooth enamel does not need to be shaved prior to the subsequent steps described below.

The next step is to determine whether the decal will be placed internal or external in the tooth restoration (504). For internal placement, it must be decided whether to add an enamel porcelain layer to the tooth restoration before application of the decal (506). In one embodiment, the enamel porcelain layer is not needed and the selected decal is placed directly on the dentin porcelain of the prepared tooth (508). Internal placement of the decal on the tooth restoration in this embodiment is similar to the process disclosed in FIG. 2. The decal is cured to the dentin porcelain (510) by any of the previously described methods. Then, a layer of enamel porcelain is placed over the dentin porcelain and decal (512). Sometimes only a small layer of dentin porcelain is required because the tooth may not be chipped as previously described and shown in FIGS. 3 and 4. In an alternative embodiment, determining to first add enamel porcelain over the dentin porcelain during step (506) necessarily requires that the selected decal be placed on the enamel porcelain (514) instead of being placed on the dentin porcelain (508). In this embodiment, the decal is cured together with the enamel porcelain and the dentin porcelain (516). A second layer of enamel porcelain is placed over the cured structure of the first layer of enamel porcelain and the decal (518).

In accordance with both of the above-described embodiments, the dentist must next determine whether to add additional coloring (520) to the tooth restoration. In the case that additional coloring is desired, an external decal is placed on the enamel porcelain (522). Next, a thin layer of enamel porcelain is placed over the external decal (524). Optionally, a layer of glaze may then be placed over the enamel porcelain (526) for further protection of the dental restoration. The external decal is placed over the enamel porcelain to further enhance the natural aesthetic look of the restored tooth. Thereafter, the prepped tooth is ready to have the veneer attached thereto (528). The restoration of the natural tooth coloration and characteristics is then complete (530) for that tooth once the veneer is attached using methods known in the art. The steps for creating a tooth restoration with a decal and a porcelain-based veneer (500) and specifically steps (502)-(526), may be repeated for multiple teeth. Often it is desirable to restore more than one tooth with veneers to ensure color consistency and characteristics among the restored teeth and non-restored teeth.

Alternatively, the process for creating a tooth restoration with a decal and a porcelain-based veneer (500) may include the step of placing the decal external to the tooth restoration (532). As shown in FIG. 5, after deciding to use an external decal (504), the selected decal is externally placed on the veneer (532) before attachment to a natural tooth. Next, the veneer and decal are fired in cured (534). Thereafter, a layer of glaze (536) is placed over the external decal for protection thereof. Accordingly, the veneer is then attached to the prepped tooth (528). The restoration of the natural tooth coloration and characteristics is then complete (530). Similarly, steps (502)-(536) may be repeated for each veneer the patient requires.

Figure 6:
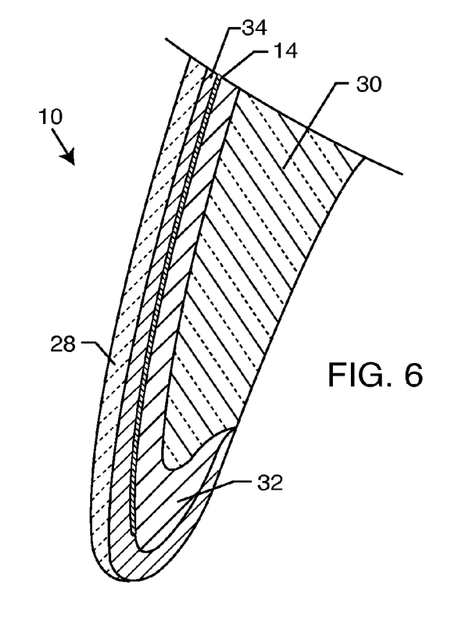
FIG. 6 is a cross-sectional view of an internal decal incorporated into the veneer-based dental restoration.
Figure 7:
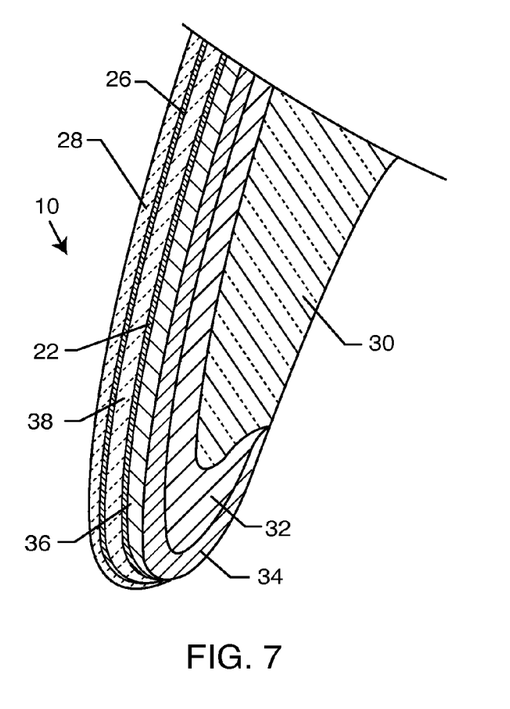
FIG. 7 is an alternative cross-sectional view of the dental restoration of FIG. 6, including an external decal for added color and characteristics.
Figure 8:
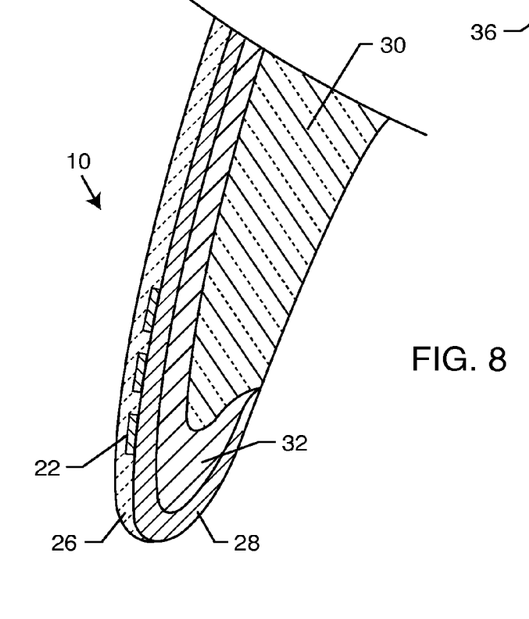
FIG. 8 is a cross-sectional view of an external decal formed on a veneer before application to the veneer-prepped tooth.

FIGS. 6-8 are cross-sectional side views of a tooth restoration 10 having a porcelain-based veneer 28. FIG. 6 illustrates the tooth restoration 10 having an internally placed decal 14. As shown, a veneer prepped tooth 30 has a dentin porcelain base 32 applied along the exterior thereof. The veneer-prepped tooth 30 may be reduced slightly in size (e.g. 1.5 millimeters) to make room for the veneer 28 and the corresponding dentin porcelain base 32, an enamel porcelain layer 34 and the decal 14. Accordingly, the decal 14 is applied to the external front layer of the dentin porcelain base 32. The enamel porcelain 34 is thereafter applied to the external surface of the decal 14 and the dentin porcelain base 32. Lastly, the veneer 28 is attached to the external portion of the enamel porcelain 34 of the tooth restoration 10 illustrated in FIG. 6. The decal 14 is visible through the enamel porcelain 34 and the veneer 28.

FIG. 7 illustrates an alternative embodiment of the tooth restoration 10 illustrated in FIG. 6. The tooth restoration 10 in FIG. 7 similarly includes the veneer-prepped tooth 30 and the dentin porcelain 32. In this embodiment, however, the enamel porcelain 34 is applied directly to the dentin porcelain 32 before application of the decal 14. The decal 14 is then applied directly to the enamel porcelain 34. Thereafter, a second layer of enamel porcelain 36 is applied over the decal 14 and any exposed portion of the enamel porcelain 34. The second layer of enamel porcelain 36 provides the necessary long term protection for the decal 14. An optional glaze 26 may be applied to the second layer of enamel porcelain 36 for further protection thereof. The glaze 26 primarily fills micro holes in the enamel porcelain and enables the dentist to polish the outer surface of the tooth restoration. The veneer 28 is then applied to the second layer of enamel porcelain 36 in a similar manner as shown and described with respect to FIG. 6. Additionally, the external decal 22 may be applied to the second layer of enamel porcelain 36 before application of the veneer 28. In this embodiment, an external enamel porcelain 38 is applied to the external decal 22, according to the steps described above. Again, the optional glaze 26 may be applied to the external enamel porcelain 38 for further protection thereof. Once the dentist determines that the appropriate colorization and characterization of the tooth are adequate, the veneer 28 is attached thereto according to the processes described above.

FIG. 8 illustrates attachment of the porcelain-based veneer 28 to the veneer-prepped tooth 30 utilizing only the external decal 22. As shown in FIG. 8, the veneer-prepped tooth 30 has the dentin porcelain base 32 applied thereto. The veneer 28, which is eventually applied directly to the dentin porcelain 32, receives the external decal 22 thereon before application to the tooth restoration 10. In this regard, the external decal 22 is applied to the exterior of the veneer 28 pre-application to the veneer-prepped tooth 30. In this embodiment, the external decal 22 and the veneer 28 are fired together in an oven. A glaze 26 is then applied to the exterior of the veneer 18 to protect the external decal 22 fired thereto. The veneer 28 having the external decal 22 and the glaze 26 thereon is thereafter attached to the dentin porcelain 32 by any method known in the art. The attached veneer 28 then displays the desired coloration and characteristics of the natural tooth via the external decal 22.

Figure 9:
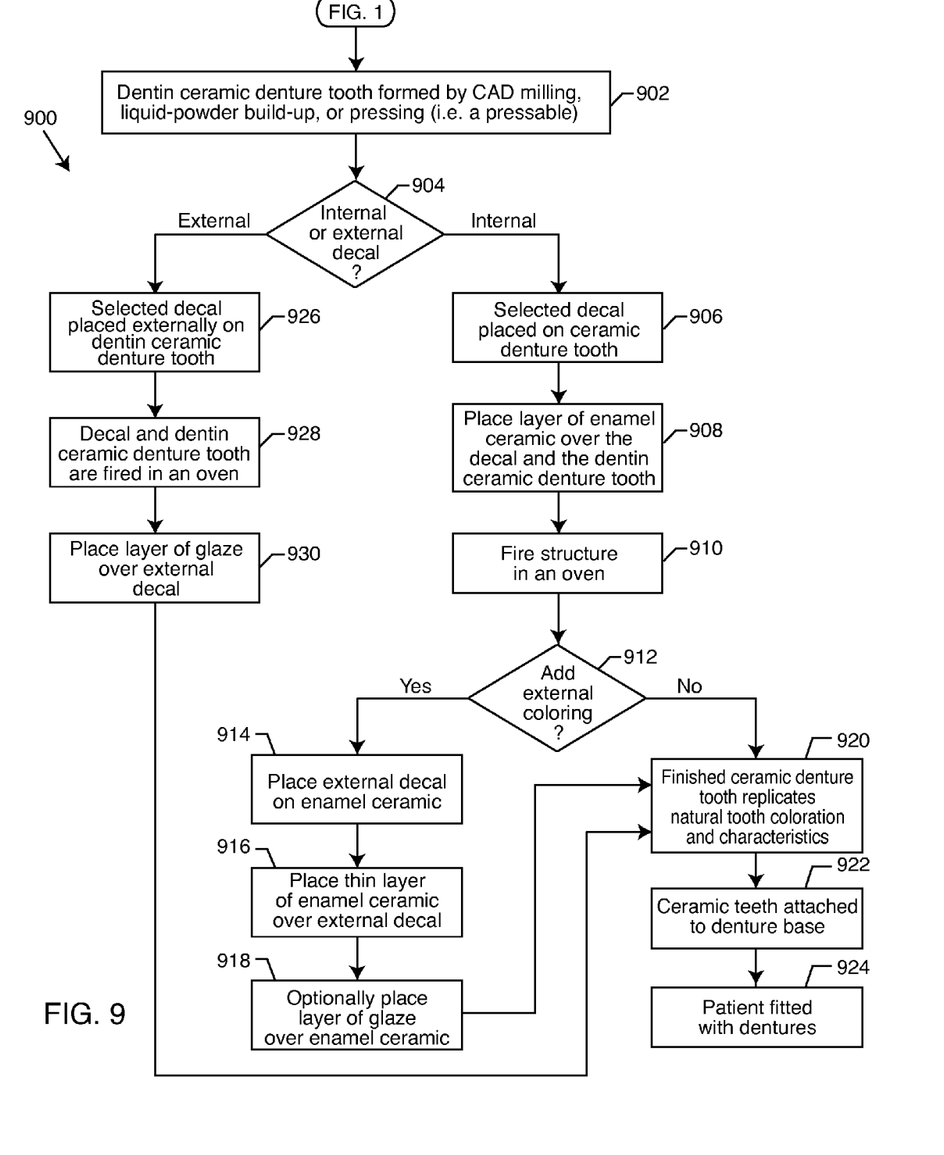
FIG. 9 is a flowchart illustrating a process of incorporating a decal into a ceramic denture tooth.

The decal 14 may also be used with ceramic teeth for placement in dentures, as generally shown in the flowchart in FIG. 9. In most instances, the steps in FIG. 9 may be accomplished by a ceramic tooth manufacturer, rather than a dentist or lab technician. Multiple decals may be needed to replicate the coloration and characteristics of multiple teeth that the dentures will replace. The use of decals in the fabrication phase of ceramic teeth for use in dentures simplifies the production process and provides more realistic dentures. The fabricated ceramic teeth contain better aesthetic coloration and characteristics.

The process for forming a ceramic denture tooth for placement in dentures (900) starts by forming a dentin ceramic denture tooth via CAD/CAM milling, liquid-powder build-up, or pressing (i.e. a pressable) (902). The next step is to determine whether the decal will be placed internal or external in the dentin ceramic denture tooth (904). Internal placement of the decal on the dentin ceramic denture tooth is similar to the process disclosed in FIG. 5. First, the selected decal is placed on the dentin ceramic denture tooth (906). Next, a layer of enamel ceramic is placed over the decal and the dentin ceramic denture tooth (908). The structure that includes the dentin ceramic denture tooth, the decal and the enamel ceramic is then fired in an oven for hardening (910). Thereafter, the ceramic tooth manufacturer or subsequent dental lab technician may determine whether or not to add external coloring (912). In the event that the external coloring is desired, an external decal is placed on the enamel colored ceramic (914). A thin layer of enamel ceramic is then placed over the external decal (916). Optionally, a layer of glaze is then placed over the enamel ceramic (918) for further protection thereof. The finished ceramic tooth should accurately replicate natural tooth coloration and characteristics (920). The necessary quantity of denture teeth are then attached to the denture base (922). Thereafter, the patient is fitted with the dentures (924) having a natural look. Alternatively, it may be decided that external coloring is not needed (912), wherein the dentures are finished (920) without any additional steps. Accordingly, the denture teeth are attached to the denture base (922) and then fitted to the patient (924).

Alternatively, it may be determined during step (904) that the decal is to be placed external in the tooth restoration. In this embodiment, the selected decal is placed externally on the dentin ceramic tooth (926). Next, the decal and the dentin ceramic tooth are fired in an oven (928). This hardens the resultant structure. A layer of glaze is then placed over the external decal (930). The finished denture tooth replicates the natural tooth coloration and characteristics of the oral cavity (920). The requisite quantity of denture teeth are then attached to the denture base (922) before the patient is fitted with the dentures (924).

The process illustrated in FIG. 9 is tremendously advantageous over current practices in that the denture teeth of the dentures include actual color and characteristics of natural teeth without spending hours in an artistic studio drawing the details. Denture teeth otherwise not having these details appear unnaturally consistently white (or a shade thereof). This is an undesirably unnatural look. The present invention eliminates the time and cost associated with an artist adding the necessary details to make the denture teeth look natural.

Figure 10:
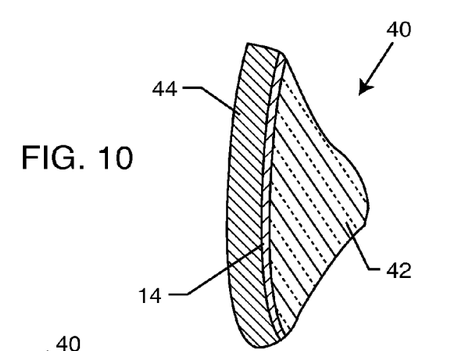
FIG. 10 is a cross-sectional view of a decal located between an enamel ceramic and a dentin ceramic in the ceramic denture tooth.
Figure 11:
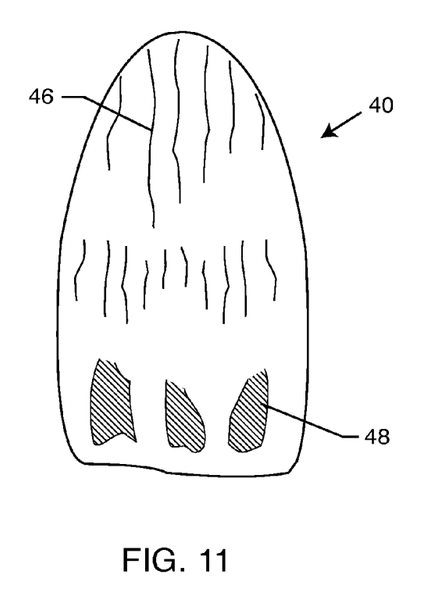
FIG. 11 is a front view of a ceramic denture tooth having a decal located therein, illustrating detail lines and lobes.
Figure 12:
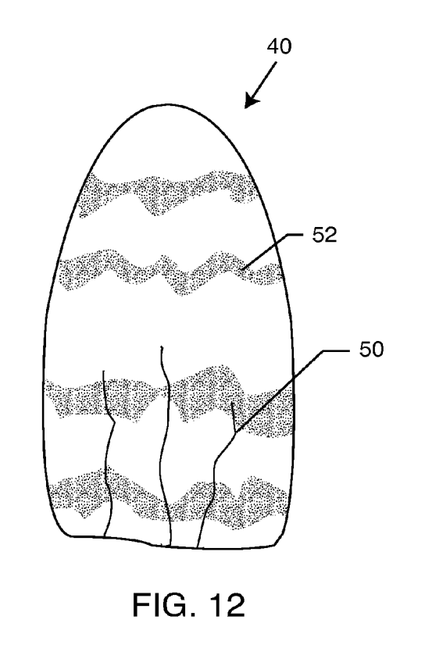
FIG. 12 is a front view of a ceramic denture tooth having a decal located therein, illustrating crazing lines and other characterizations.

FIGS. 10-12 illustrate a sample denture tooth 40 for placement in dentures. FIG. 10 illustrates a cross-sectional view of the denture tooth 40 comprising a dentin base 42 having the decal 14 placed thereover and protected by an enamel material 44. The stylizations of the internal decal 14 placed between the dentin base 42 and the enamel material 44 are visible through the enamel material 44. FIG. 11 illustrates a front view of the denture tooth 40 having a plurality of details therein. For example, the denture tooth 40 includes a set of detail lines 46 and lobes 48. As more specifically shown in FIG. 12, the detail lines 46 may include a set of crazing lines 50 or white stains 52. In each of the embodiments illustrated in FIGS. 10-12, the denture tooth 40 has the decal 14 placed internally. The details illustrated in FIGS. 11 and 12 may come in many different types of stylizations, as previously described and listed. Moreover, the decal 14 may be placed externally, as described above. The decal may also be used in dentures with composite resin-based teeth in addition to the ceramic-based teeth.

Figure 13:
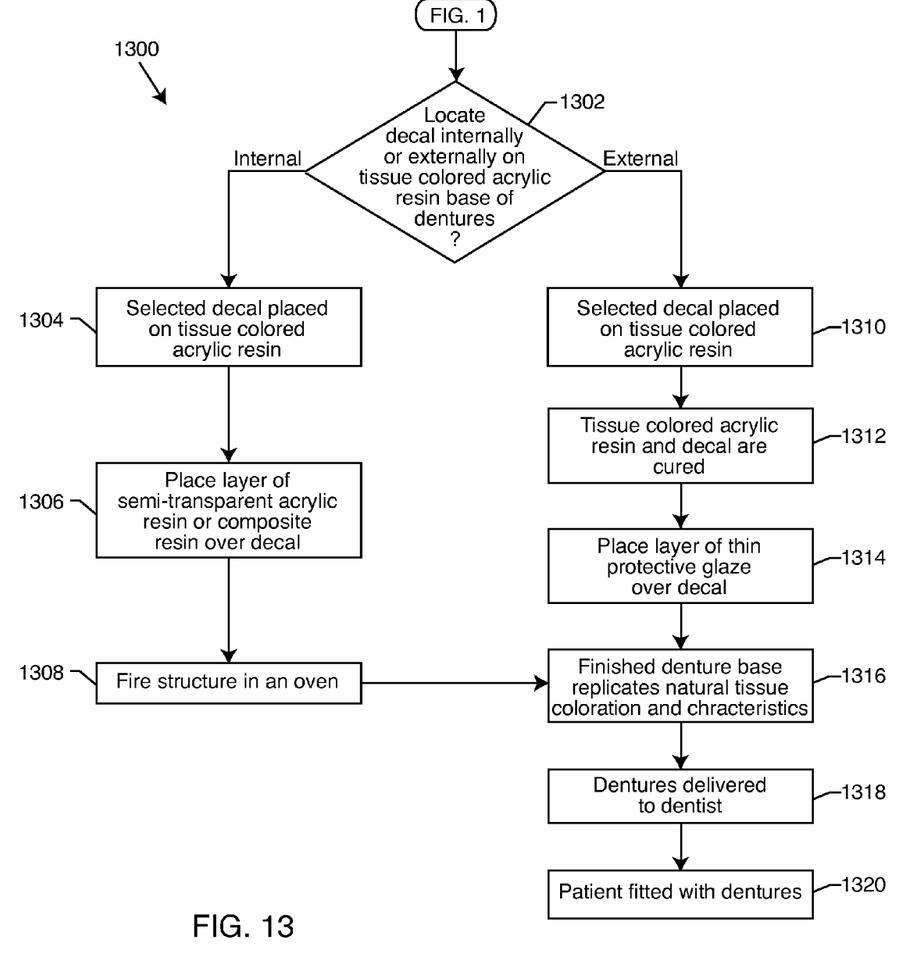
FIG. 13 is a flowchart illustrating the process of incorporating a decal into an acrylic resin representing tissue in dentures.

FIG. 13 illustrates the general process for incorporating a decal in a dental appliance for replicating the natural color and characteristics of oral tissue (1300). First, a lab technician must determine whether the decal is to be located internally or externally on a tissue colored acrylic resin base (1302). An internally located decal is placed directly on the tissue colored acrylic resin (1304) in the dental appliance. These decals may, alternatively, be used to represent soft tissue coloration and characteristics and can be used in conjunction with veneers, crowns, bridges and other implants. The decals mimic the tissue stylizations applied to dental restorations when soft tissue prosthesis is necessary. A layer of semi-transparent acrylic resin or composite resin is then placed over the decal (1306). The tissue colored acrylic resin base and the decals are then fired in an oven (1308). External placement of the decal requires that the selected decal be placed on the tissue colored acrylic resin base (1310). This structure is then also hardened by curing (1312). Next, a thin layer of protective glaze is placed over the external decal (1314). The protective glaze provides insulation of the decal from the environment and protects against wear. The result of steps (1308) and (1314) is that the finished dental appliance replicates the natural tissue coloration and characteristics of the oral cavity (1316). The finished structure is then delivered to the dentist (1318) to be fitted to the patient (1320). In this embodiment, the internal or external decals mimic the oral tissue coloring, which may comprise blood vessels, tissue covering, musculature areas, tendons, tissue colors or bony anatomy changes. The steps disclosed in FIG. 13 may also be combined with those steps disclosed in FIG. 9 to provide dentures having both natural looking teeth (FIGS. 10-12) and oral tissue (FIGS. 14-15).

Figures 14, 15:
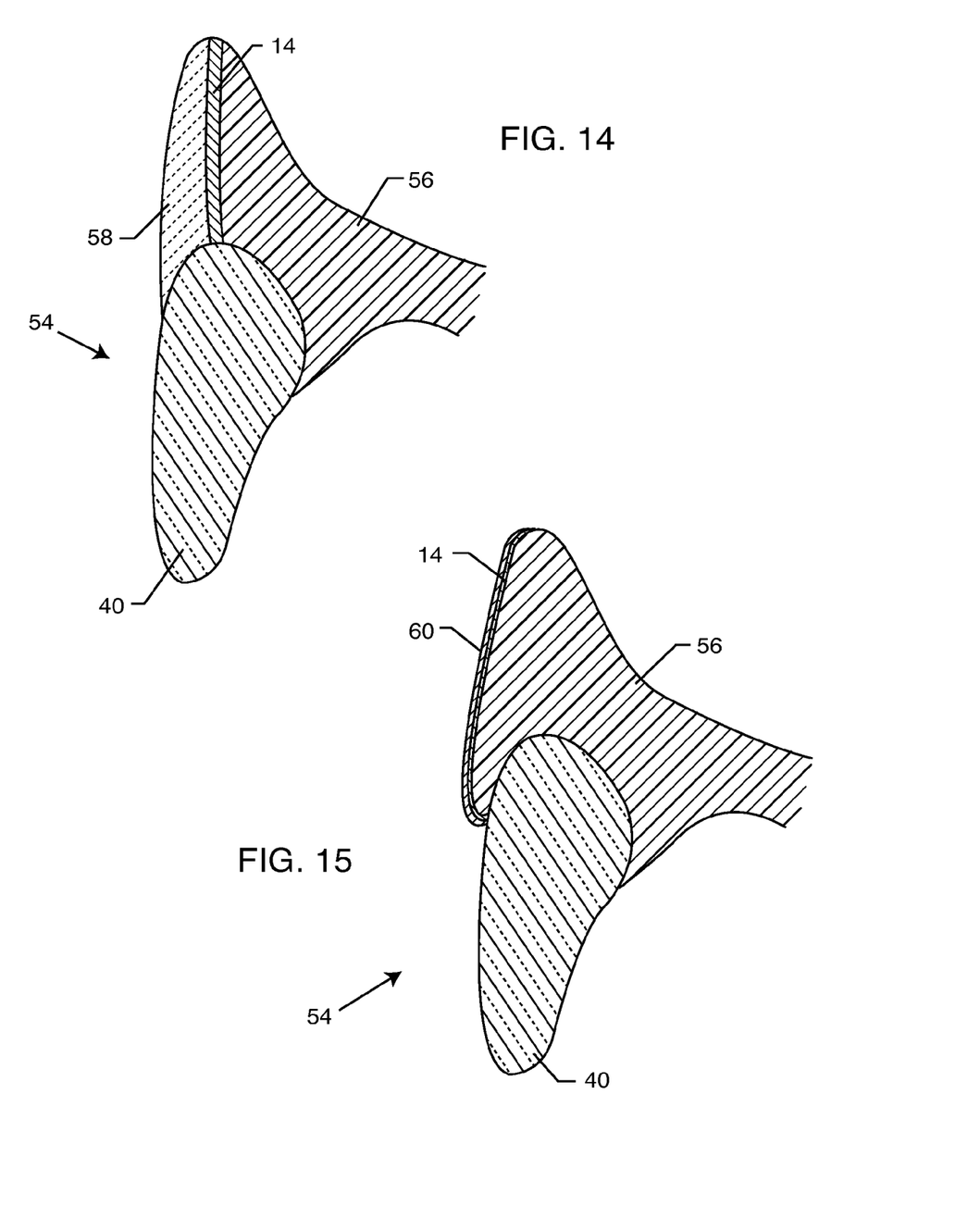
FIG. 14 is a cross-sectional view of an internally placed decal representing the tissue area of dentures.
FIG. 15 is a cross-sectional view of an externally placed decal representing the tissue area of dentures.

FIGS. 14 and 15 illustrate the internal and external placement, respectively, of the decal 14 in the oral tissue area of dentures. FIGS. 14 and 15 are a cross-sectional view of a denture 54, generally. Accordingly, the dentures 54 include a tissue colored acrylic resin 56 adjacent to the previously described denture tooth 40. In FIG. 14, the decal 14 is placed internal in the denture 54 as sandwiched between the tissue colored acrylic resin 56 and a semi-transparent tissue colored acrylic resin 58. The semi-transparent tissue colored acrylic resin 58 allows the details of the decal 14 to be seen externally. Thus, the natural tissue coloration the decal 14 aims to display is visible. Alternatively, in FIG. 15 the decal 14 is external to the tissue colored acrylic resin 56 and is protected by a protective layer 60. Preferably the protective layer 60 is the previously described glaze.

In general, the decals of the present invention are fabricated from a photo, captured image or drawing to aesthetically mimic the internal and/or external coloration and characteristics of natural teeth and the internal and/or external coloration and characteristics of natural tissue surrounding tooth areas, such as papillae and mucosal tissue. The fabrication of the composite resin restorations, either directly or indirectly, includes placing a decal or part of a decal in a composite resin or ceramic fabrication to mimic the internal and external anatomical coloration of the oral cavity. Mimicking the natural color stylizations allows dentists to offer patients dental restorations having tooth and tissue coloration and characteristics, within a thin dimension, that best matches the oral cavity aesthetics of the patient.

The decals can create a three-dimensional natural looking tooth restoration by placing the decals in multiple layers of composite resin or ceramic material. Alternatively, the multiple decals may be stacked on one another or placed intermittently in the front, bottom or rear portions of the tooth restoration. The key aspect of the present invention is that the decal replaces any need for drawing tooth or tissue coloration and characteristics to the dental restoration. The composite resin, ceramic, porcelain or glaze protect the decal to increase durability. The decals described herein can be placed in areas where composite resin layering, ceramic layering and acrylic resin layering are being used. Such layering may be used in the fabrication of denture teeth, tooth restorations or mucosal tissue replication. The present invention may also be used with partial veneers, crown and bridge applications and chipped or broken teeth as well as non-prepared teeth for veneering purposes.

Although several embodiments have been described in some detail for purposes of illustration, various modifications may be made to each without departing from the scope and spirit of the invention. Accordingly, the invention is not to be limited, except as by the appended claims.

What is claimed is:

1. A process for making a dental restoration, comprising the steps of:
    creating an image including tooth structure, tooth coloration, enamel, dentin, crazing lines, stains, bony coloration, hyper-calcification, mucosal tissue, gum tissue, or blood vessels so as to be similar in appearance to at least a portion of a natural tooth or oral cavity tissue of a patient;
    sizing the image to correspond to a tooth or tooth restoration base of a patient;
    printing the image as a decal;
    attaching the decal to a dental restoration base or a tooth of the patient; and
    conditioning the decal to create a finished dental restoration.

2. The process of claim 1, wherein the creating step includes the step of capturing a photograph of a tooth, oral cavity tissue or a model of a tooth.

3. The process of claim 2 including the step of modifying the photograph with a computer-aided software program.

4. The process of claim 1 wherein the creating step includes the step of creating a computer-generated image.

5. The process of claim 1 wherein the creating step includes the step of creating a drawing.

6. The process of claim 1, wherein the creating step includes the step of fabricating a stock of a plurality of images similar in appearance to at least a portion of a natural tooth or oral cavity tissue.

7. The process of claim 6, including the steps of selecting an image from the stock of the plurality of images and printing the image onto a decal.

8. The process of claim 7, including the step of colorizing the image to match the desired tooth or natural oral cavity characteristics of the patient.

9. The process of claim 1, including the step of creating a distributable picture of the image matching the decal.

10. The process of claim 1, wherein the conditioning step includes the step of curing the decal and the dental restoration base with a high intensity light or firing the decal and the dental restoration base in an oven.

11. The process of claim 10, wherein the curing of the decal and the dental restoration base with high intensity light occurs chair side of the patient.

12. The process of claim 1, including the step of placing a sealant over the decal and at least a portion of the dental restoration base.

13. The process of claim 12, wherein the sealant comprises a composite resin, a semi-transparent acrylic resin, a protective layer, or a glaze.

14. The process of claim 1, including the steps of attaching a secondary decal on the tooth restoration base or tooth, the secondary decal having printed thereon an image of tooth structure, tooth coloration, enamel, dentin, crazing lines, stains, bony coloration, hyper-calcification, mucosal tissue, gum tissue, or blood vessels so as to mimic at least a portion of a natural tooth or oral cavity tissue.

15. The process of claim 14, including the step of placing a sealant over the secondary decal and at least a portion of the dental restoration base, wherein the sealant comprises a composite resin, a semi-transparent acrylic resin, a protective layer, or a glaze.

16. The process of claim 1, wherein the dental restoration base comprises a composite resin, an acrylic resin, a ceramic or a semi-transparent acrylic resin.

17. A process for making a dental restoration, comprising the steps of:
    creating an image including tooth structure, tooth coloration, enamel, dentin, crazing lines, stains, bony coloration, hyper-calcification, mucosal tissue, gum tissue, or blood vessels so as to be similar in appearance to at least a portion of a natural tooth or oral cavity tissue of a patient;
    sizing the image to correspond to a tooth or tooth restoration base of a patient;
    printing the image as a decal;
    attaching the decal to a dental restoration base or a tooth of the patient; and
    curing the decal and the dental restoration base with a high intensity light or firing the decal and the dental restoration base in an oven to create a finished dental restoration;
    wherein the creating step includes the step of capturing a photograph of a tooth, oral cavity tissue or a model of a tooth, creating a computer-generated image, or creating a drawing.

18. The process of claim 17, including the step of modifying the photograph with a computer-aided software program.

19. The process of claim 17, wherein the creating step includes the step of fabricating a stock of a plurality of images similar in appearance to at least a portion of a natural tooth or oral cavity tissue.

20. The process of claim 19, including the steps of selecting an image from the stock of the plurality of images and printing the image onto a decal.

21. The process of claim 17, including the step of colorizing the image to match the desired tooth or natural oral cavity characteristics of the patient.

22. The process of claim 17, including the step of creating a distributable picture of the image matching the decal.

23. The process of claim 17, wherein the curing of the decal and the dental restoration base with high intensity light occurs chair side of the patient.

24. The process of claim 17, including the step of placing a sealant over the decal and at least a portion of the dental restoration base.

25. The process of claim 24, wherein the sealant comprises a composite resin, a semi-transparent acrylic resin, a protective layer, or a glaze.

26. The process of claim 17, including the steps of attaching a secondary decal on the tooth restoration base or tooth, the secondary decal having printed thereon an image of tooth structure, tooth coloration, enamel, dentin, crazing lines, stains, bony coloration, hyper-calcification, mucosal tissue, gum tissue, or blood vessels so as to mimic at least a portion of a natural tooth or oral cavity tissue.

27. The process of claim 26, including the step of placing a sealant over the secondary decal and at least a portion of the dental restoration base, wherein the sealant comprises a composite resin, a semi-transparent acrylic resin, a protective layer, or a glaze.

28. The process of claim 17, wherein the dental restoration base comprises a composite resin, an acrylic resin, a ceramic or a semi-transparent acrylic resin.

29. A process for making a dental restoration, comprising the steps of:
creating a stock of a plurality of images including tooth structure, tooth coloration, enamel, dentin, crazing lines, stains, bony coloration, hyper-calcification, mucosal tissue, gum tissue, or blood vessels so as to be similar in appearance to at least a portion of a natural tooth or oral cavity tissue of a patient;
selecting an image from the stock of the plurality of images an image;
colorizing the image to match the desired tooth or natural oral cavity characteristics of the patient;
sizing the image to correspond to a tooth or tooth restoration base of a patient;
printing the image as a decal;
attaching the decal to a dental restoration base or a tooth of the patient;
placing a sealant over the decal and at least a portion of the dental restoration base; and
curing the decal and the dental restoration base to create a finished dental restoration;
wherein the creating step includes the step of capturing a photograph of a tooth, oral cavity tissue or a model of a tooth, creating a computer-generated image, or creating a drawing.

30. The process of claim 29, including the step of modifying the photograph with a computer-aided software program.

31. The process of claim 29, including the step of creating a distributable picture of the image matching the decal.

32. The process of claim 29, wherein the curing of the decal and the dental restoration base with high intensity light occurs chair side of the patient.

33. The process of claim 29, including the steps of:
attaching a secondary decal on the tooth restoration base or tooth, the secondary decal having printed thereon an image of tooth structure, tooth coloration, enamel, dentin, crazing lines, stains, bony coloration, hyper-calcification, mucosal tissue, gum tissue, or blood vessels so as to mimic at least a portion of a natural tooth or oral cavity tissue; and
placing a sealant over the secondary decal and at least a portion of the dental restoration base.

34. The process of claim 29, wherein the dental restoration base comprises a composite resin, an acrylic resin, a ceramic or a semi-transparent acrylic resin.

* * * * *